United States Patent
Mandel et al.

(10) Patent No.: US 6,506,213 B1
(45) Date of Patent: Jan. 14, 2003

(54) MANUFACTURING ORTHOPEDIC PARTS USING SUPERCRITICAL FLUID PROCESSING TECHNIQUES

(75) Inventors: Frederick S. Mandel, Chagrin Falls, OH (US); J. Don Wang, Brecksville, OH (US)

(73) Assignee: Ferro Corporation, Cleveland, OH (US)

( * ) Notice: Subject to any disclaimer, the term of this patent is extended or adjusted under 35 U.S.C. 154(b) by 0 days.

(21) Appl. No.: 09/658,250

(22) Filed: Sep. 8, 2000

(51) Int. Cl.[7] .............................. A61F 2/02; C08F 6/10
(52) U.S. Cl. ..................... 623/16.11; 523/342
(58) Field of Search .................. 424/93.1, 424, 424/425, 426, 443; 523/444, 342; 264/121; 623/18.11, 16.11, 66

(56) References Cited

U.S. PATENT DOCUMENTS

| | | |
|---|---|---|
| 5,082,803 A | 1/1992 | Sumita |
| 5,294,393 A * | 3/1994 | Toki et al. .................. 264/121 |
| 5,399,597 A | 3/1995 | Mandel et al. |
| 5,548,004 A | 8/1996 | Mandel et al. |
| 5,698,163 A | 12/1997 | Mandel |
| 5,989,289 A | 11/1999 | Coates et al. |
| 5,993,747 A | 11/1999 | Mandel |
| 6,005,162 A | 12/1999 | Constantz |
| 6,054,103 A | 5/2000 | Mandel |
| 6,333,029 B1 * | 12/2001 | Vyakarnam et al. ....... 424/93.1 |

FOREIGN PATENT DOCUMENTS

WO   WO98/51347   11/1998

OTHER PUBLICATIONS

U.S. patent application Ser. No. 09/315,616, Mandel, filed May 20, 1999.

F. Mandel, Manufacturing of Specialty Materials in Supercritical Fluid Carbon Dioxide, Inorganica Chimicia Acta 294 (1999) 214–223.

K. Uhrich, Polymeric Systems for Controlled Drug Release, Journal of the American Chemical Society (1999).

* cited by examiner

*Primary Examiner*—David J. Isabella
(74) *Attorney, Agent, or Firm*—Rankin, Hill, Porter & Clark LLP

(57) ABSTRACT

Orthopedic parts are manufactured using supercritical fluid processing techniques in which starting materials and a process medium are mixed in a reactor to form a supercritical fluid slurry. The starting materials include a source of calcium ions and a polymer matrix for the calcium ions. The process medium preferably is carbon dioxide which is supplied to the reactor in a supercritical state or which is heated and pressurized in the reactor to attain a supercritical state. A conduit connects the reactor to a mold that has a cavity of a desired shape for an orthopedic part. A flush valve interconnects the bottom of a reactor and the conduit. When the flush valve is opened, the slurry is directed through the conduit into the mold where solidification occurs very rapidly. The resultant product is a strong, porous structure that simulates autogenic

17 Claims, 1 Drawing Sheet

MANUFACTURING ORTHOPEDIC PARTS USING SUPERCRITICAL FLUID PROCESSING TECHNIQUES

BACKGROUND OF THE INVENTION

1. Field of the Invention

The invention relates to the use of supercritical fluid processing techniques to manufacture a variety of orthopedic parts such as bone grafts that can be used as spinal implants.

2. Description of the Prior Art.

There is a need for orthopedic parts such as bone prostheses, spinal implants, and the like. For example, in the field of spinal surgery, removal of all or a portion of a damaged intervertebral disc requires that the resulting space be filled to prevent disc space collapse and to promote fusion of the adjacent vertebrae across the disc space. Desirably, the space will be filled with an implant that will have adequate strength to withstand loads imposed by the vertebrae and which will permit bone ingrowth. Although implants made of a metal such as titanium alloy have adequate strength, they have various drawbacks such as a tendency to have relatively long fusion times. Implants made of bone grafts are desirable because bone grafts are biological materials which are replaced over time with the patient's own bone, via the process of creeping substitution. Over time a bone graft virtually disappears, unlike a metal implant which persists indefinitely.

Unfortunately, bone grafts present several disadvantages. Autogenic bone is available only in limited quantities. The additional surgery also increases the risk of infection and blood loss and may reduce structural integrity at the donor site. The graft harvesting surgery is alleged to cause extreme pain that may exceed the pain of the fusion surgery. Allogenic and xenogenic bone grafts are undesirable because they involve the implantation of a bone of foreign origin into the body, with attendant risks of infection or rejection. Desirably, a bone substitute would be available that would have the advantages of autogenic bone, without the drawbacks of allogenic or xenogenic bone.

SUMMARY OF THE INVENTION

In response to the foregoing concerns, the present invention provides a technique for the manufacture of orthopedic parts such as bone grafts that have the desirable characteristics of autogenic bone, but without the drawbacks of allogenic bone or xenogenic bone. Such parts can be provided with the porosity and strength characteristics of either cortical bone or cancellous bone, as required.

The invention includes a reactor that has a mixer, a mold that has a cavity of a desired shape, and a conduit that connects the reactor and the mold. The reactor is charged with starting materials that will produce an orthopedic part of desired strength characteristics. The starting materials include a source of calcium ions and a polymer or multiple polymers that forms a matrix for the calcium source. A process medium is added to the reactor. In the preferred embodiment, the process medium is liquid $CO_2$. After the reactor is sealed, the process medium is heated and pressurized to form a supercritical fluid. The heated and pressurized ingredients are mixed in the reactor for a period of time sufficient to form them into a homogeneous, gas-saturated suspension, or supercritical fluid slurry. The supercritical fluid slurry then is transferred from the reactor into the mold through the conduit. The slurry solidifies quickly in the mold to form a strong, dense product having a porous structure. Typically, the product will have a high percentage of calcium, will be porous with 100% interconnectivity of pores (i.e., without isolated pores), and will have pore sizes on the order of 300–400 mircrons.

The parameter of the process and the equipment for carrying it out can be varied to produce products having different characteristics. For example, the starting materials and their relative proportions, the process medium used and the temperature and pressure in the reactor, the mixing time, the pressure drop that occurs during material transfer, the temperature of the conduit, the shape of the mold, and the temperature of the mold can be varied. If desired, an orifice or a nozzle having multiple openings can be disposed in the conduit to control the flow rate and the size of the particles. The size of the pores in the finished product can be controlled by varying the density of the supercritical process medium and by the rate at which depressurization occurs. By using the present invention, a variety of orthopedic parts that simulate autogenic bone and which have different porosity and strength characteristics can be obtained.

DESCRIPTION OF THE PREFERRED EMBODIMENT

Figure 1:
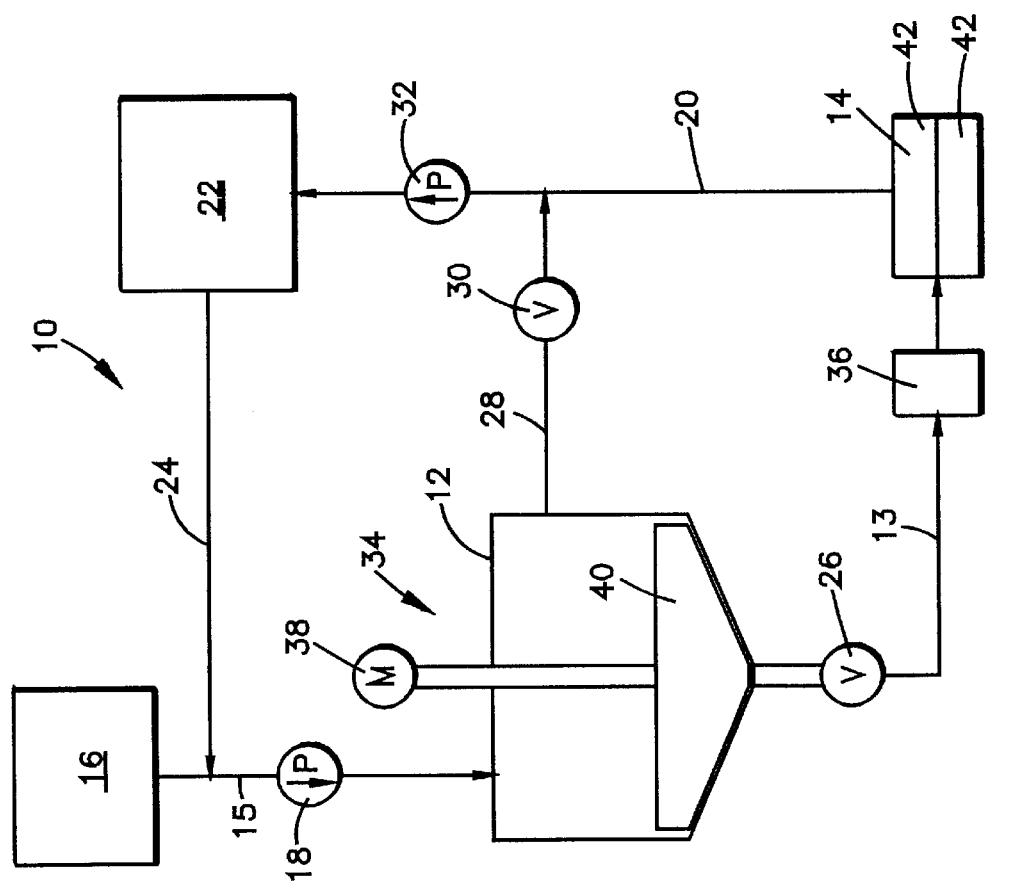
FIG. 1 is a schematic view of apparatus suitable for practicing the present invention.

Referring now to FIG. 1, apparatus for practicing the present invention is indicated generally by the reference numeral 10. The apparatus 10 is described in U.S. Pat. No. 5,399,597, entitled Method of Preparing Coating Materials, issued Mar. 21, 1995 to Frederick S. Mandel, et al. Reference also is made to U.S. Pat. No. 5,698,163, entitled Control System for Processes Using Supercritical Fluids, issued Dec. 16, 1997 to Frederick S. Mandel, for a description of a control system for the apparatus 10. Additional details of the apparatus 10 can be found in U.S. Pat. No. 6,054,103, entitled Mixing System for Processes Using Supercritical Fluids, issued Apr. 25, 2000 to Frederick S. Mandel; U.S. application Ser. No. 09/315,616, entitled Delivery System for Processes Using Supercritical Fluids, filed May 20, 1999 by Frederick S. Mandel; and U.S. Pat. No. 5,993,747, entitled Mixing System for Processes Using Supercritical Fluids, issued Nov. 30, 1999 to Frederick S. Mandel. The disclosures of all of the patents and applications referred to in this paragraph are incorporated in the present specification by reference.

Continuing to refer to FIG. 1, the apparatus 10 includes a reactor 12 that is connected by conduit 13 to a mold 14. Although one mold 14 is shown, it is possible, indeed desirable, to simultaneously use a number of molds 14, each supplied with a conduit 13. Connected by conduit 15 to the reactor 12 is a source 16 of a process medium such as liquid carbon dioxide. The process medium preferably is fed under pressure into reactor 12 using a compressor or liquid pump 18. The mold 14 is connected by conduit 20 to a return tank 22. The return tank 22 is connected by conduit 24 to the source 16 of the process medium.

Reactor 12 includes, preferably at its base, a valve 26 for facilitating the emptying of the contents of the reactor 12 into the mold 14. A conduit 28 connects the top portion of the reactor 12 to conduit 20. A control valve 30 is included in conduit 28. A compressor 32 is included in conduit 20. Compressor 32 compresses and transfers gas emanating from the reactor 12 or the mold 14 into the return tank 22.

Reactor 12 includes a sealable opening or access port (not shown) that permits material to be charged into the reactor 12. Reactor 12 also includes a mechanical stirring device 34 for mechanically agitating and stirring the contents of reactor 12 so as to form a homogeneous mixture. Preferably, the access port is equipped with a quick-opening, breech-lock system that requires no hand tools to open and close. Also, reactor 12 preferably includes a feed port having a valve (not shown) that facilitates the quick addition of minor amounts of material (e.g., polymer) to the reactor 12 once it has been pressurized.

Reactor 12 and mold 14 preferably are made of stainless steel. However, it will be appreciated that a number of alternative materials may be utilized, such as, for example, nickel-coated carbon steel or carbon steel vessels having chemically inert inserts or liners. A particularly desirable reactor 12 is shown in U.S. Pat. No. 6,054,103, referred to previously.

The length of conduit 13 is minimized as much as possible. Conduit 13 can be in the form of a constant-diameter tubing. Alternatively, an orifice can be disposed in the conduit 13 just prior to mold 14. In another alternative, a header 36 can be disposed in conduit 13 just prior to mold 14. The header 36 includes a nozzle having multiple openings through which the homogeneous mixture is sprayed. Any number of nozzle openings may be employed to spray the slurry. Of course, it will be appreciated that the selection of the proper nozzle will be a function of various parameters, such as, for example, the pressure employed in reactor 12, the size of particles and flow rates desired, and the starting materials and process medium being used.

Typically, an orifice in the conduit 13 or the openings in a spray nozzle in the header 36 have a diameter of from about 0.00254 centimeter to about 2.54 centimeters, preferably from about 0.0127 centimeter to about 1.27 centimeters, and more preferably from about 0.0254 centimeter to about 0.254centimeter. Examples of suitable spray nozzles are hydraulic atomizing nozzles sold by Spraying Systems Co. of Wheaton, Ill. Reference is made to application Ser. No. 09/315,616, referred to previously, for a disclosure of a particularly desirable control valve 26 and header 36.

Mechanical stirring device 34 comprises an electric motor 38 that drives a mixer 40. Mixer 40 may comprise any number of conventional mixing devices. The selection of the proper mixer will be a function of various parameters, such as, for example, the size of motor 38, the materials being mixed, the configuration of the reactor 12, the process medium being utilized and the pressure employed in vessel 12. An example of a suitable mixer 40 is a Cowles blade mixer sold by Indco, Inc. of New Albany, Ind. Reference is made to U.S. Pat. No. 6,054,103, referred to previously, for a disclosure of a particularly effective mixer 40. It will be appreciated that the present invention preferably provides for both distributive and dispersive mixing, thus there is no need to premix the materials under high shear.

Figure 2:
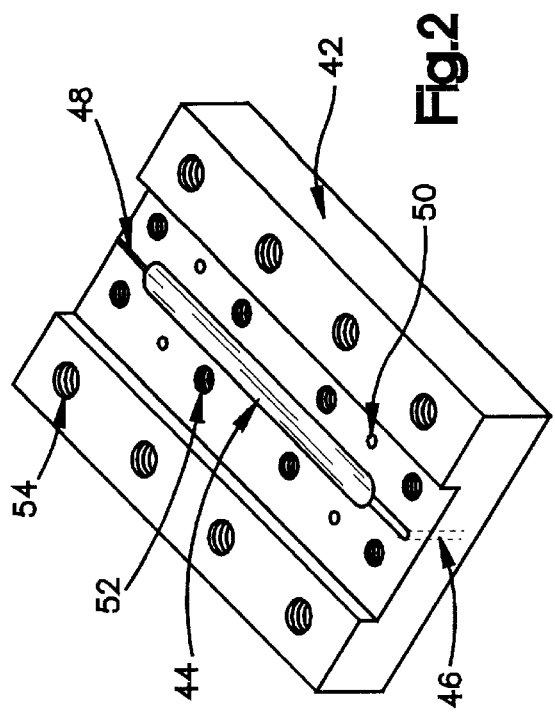
FIG. 2 is a perspective view of a mold half for manufacturing an orthopedic part having a simple shape.

Referring now to FIG. 2, a portion of mold 14 is indicated by the reference numeral 42. The portion 42 is one-half of the mold 14, the other half not being shown for purposes of clarity of illustration. The mold half 42 includes a part cavity 44 of a desired shape which, in the embodiment illustrated, is a half-cylinder with rounded ends. The cavity of an assembled mold 14 thus will produce a cylinder with rounded ends. The mold half 42 includes an inlet 46 that is in fluid communication with the conduit 20. Several threaded openings 52 enable the mold to be mounted to any suitable structure.

Figure 3:
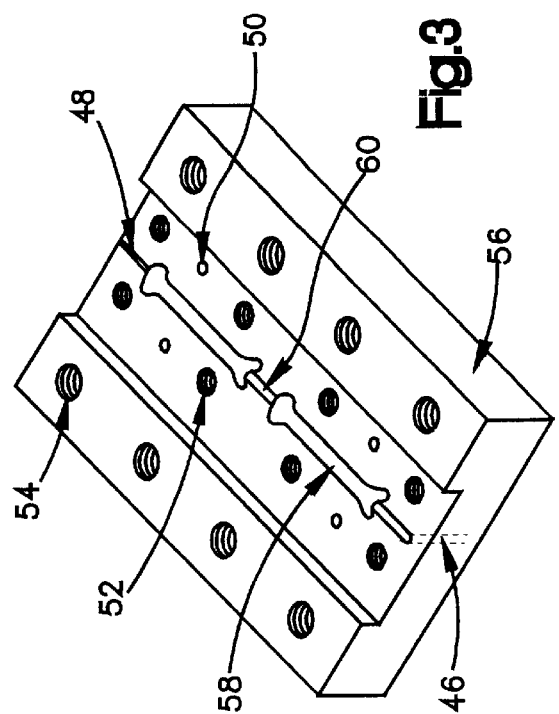
FIG. 3 is a perspective view of a mold half for manufacturing an orthopedic part having a more complex shape.

Referring now to FIG. 3, another mold half 56 is illustrated. The mold half 56 includes two parts cavities 58, each of a more complex shape than the part cavity 44. The cavities 58 are half-cylinders that have enlarged, generally rounded ends. Although the cavities 58 are identical, they can be formed into different shapes, if desired. The cavities 58 are connected by a channel 60. In all other respects, the mold half 56 is identical to the mold half 42, and like reference numerals are carried over from FIG. 2 to illustrate comparable elements. It is expected that the cavities 44, 58 can be formed in any desired size or shape by appropriate machining techniques, such as EDM. Accordingly, the mold 14 can be used to produce an orthopedic part precisely suited to patient's needs, regardless of the complexity of the part. In cases where such custom fitting is not required, the cavities 44, 58 can be formed in a variety of standard sizes and shapes to produce an inventory of orthopedic. parts for a surgeon or hospital.

Apparatus 10 is employed in accordance with the present invention by first charging the starting materials for the orthopedic part that one desires to produce into the reactor 12. Reactor 12 then is sealed and isolated. The process medium from source 16 then is fed into reactor 12 via conduit 15 until a suitable quantity has been introduced into reactor 12. A critical temperature can be attained by heating reactor 12, heating the liquid/gas stream as it enters reactor 12, by agitating reactor 12, or by combinations of these techniques. The pressure and temperature in reactor 12 converts the process medium into a supercritical fluid.

Reactor 12 is maintained at an internal temperature of about −85° C. to about 200° C. When utilizing $CO_2$ as a process medium, a temperature of about 15° C. to about 160° C. is employed, and preferably about 20° C. to about 150° C., and more preferably about 31° C. to about 100° C. The particular temperature utilized will be a function of various variables such as, for example, the gas utilized, the composition of the starting materials, the pressures employed and equipment configurations. Pressure from about 23.80 bar to about 1360 bar may be utilized. When employing a gas such as $CO_2$, a pressure of about 37.41 bar to about 476 bar is utilized, and preferably about 64.6 bar to about 340 bar, and more preferably about 73 bar to about 306 bar. The particular pressure utilized will be a function of such variables as the temperature of the reactor 12 and the particular process medium utilized.

Once reactor 12 has been heated and pressurized, motor 38 is energized and the starting materials and the supercritical fluid are thoroughly mixed to form a homogeneous, gas-saturated suspension, otherwise referred to as a supercritical fluid slurry. Preferably, reactor 12 is held below the melting point of the materials being processed. The temperature in reactor 12 preferably is in the range of from about 5 degrees below the $T_g$ (i.e., glass transition temperature) of at least one of the materials being processed up to about the melting point of such one material. In the case of an amorphous material, "melting point" means the temperature at which the material becomes wholly fluid. It is believed that a supercritical fluid will suppress the $T_g$ of most materials. In order to attain the desired temperature in reactor 12, reactor 12 may be equipped with heat exchangers or other suitable heating/cooling means.

The starting materials are mixed in reactor 12 for a period of about 1 to about 480 minutes, preferably about 5 to about 300 minutes and more preferably from about 30 to about 240 minutes. The viscosity of the supercritical fluid slurry is a function of the temperature and the density of the process medium. Once the starting materials have been thoroughly mixed, valve 26 is opened and maintained in the open position until such time as mold 14 (which is maintained at a lower pressure than reactor 12) has been filled and reactor 12 has been emptied of its contents. It has been found that the best results are obtained if the flow within conduit 13 upstream of the header is entirely laminar. Laminar flow is induced via increasing the pressure drop to greater than 1.24 bar. In order to produce fine powders, a pressure drop of less than 1.24 bar is required. Once mold 14 has been filled substantially and all of the starting materials have been transferred, valve 30 is opened in order to depressurize reactor 12 and permit the flow of gaseous process medium into return tank 22. The recycled process medium is made available for purposes of reuse by being transferred via conduit 24 to conduit 15.

While the slurry is being transferred to mold 14, mold 14 is held at a constant pressure via use of back pressure regulation. Preferably the pressure in mold 14 is lower than that in the reactor 12 so that the slurry enters mold 14 at a very high rate. Mold 14 is maintained at a starting temperature of about −85° C. to about 220° C., preferably about −18° C. to about 160° C., and more preferably about 0° C. to about 130° C. As with reactor 12, in order to maintain the desired temperature in mold 14, heat exchangers or other cooling/heating devices may be necessary. Preferably, mold 14 is maintained at a temperature below the melting point of the materials being processed. Mold 14 is maintained at a pressure of about 0 bar to about 68.0 bar, preferably about 6.8 bar to about 136.0 bar, and more preferably about 10.20 bar to about 687 bar. The particular pressure and temperature utilized in mold 14 are a function of various variables, such as the particular process medium utilized and the composition of the starting materials.

The present invention uses a process medium that is capable of achieving a supercritical state. As used herein, the phrase "supercritical fluid" means a material that at specific temperatures and pressures no longer displays the properties of either a gas or a liquid. Examples of potential supercritical fluids suitable for use-with the present invention include carbon dioxide, water, nitrous oxide, methane, ethane, ethylene, propane, pentane, benzene, methanol ethanol isopropanol, various fluorocarbons such as cholrotrifluoromethane and monofluoromethane, toluene, pyridine, cyclohexane, decalin, cyclohexanol, o-xylene, and tetralin. The critical properties for these compounds are set forth below. The present invention contemplates the use of these compounds either by themselves or in combination. Additionally, it will be appreciated that solvents such as acetone, ketones, or ethers may be utilized in conjunction with the compounds listed below. Generally, however, the use of such solvents is not desired.

| Compound | Critical Temperature (° C.) | Critical Pressure (bar) |
| --- | --- | --- |
| $CO_2$ | 31.3 | 72.9 |
| $H_2O$ | 374.15 | 218.3 |
| $N_2O$ | 36.5 | 71.7 |
| Methane | −82.1 | 45.8 |
| Ethane | 32.28 | 48.1 |
| Ethylene | 9.21 | 49.7 |
| Propane | 96.67 | 41.9 |
| Pentane | 196.6 | 33.3 |
| Benzene | 288.9 | 48.8 |
| Methanol | 240.5 | 78.9 |
| Ethanol | 243.0 | 63.0 |
| Isopropanol | 235.3 | 47.0 |
| Isobutanol | 275.0 | 42.4 |
| Chlorotrifluoromethane | 28.0 | 38.7 |
| Monofluoromethane | 44.6 | 58.0 |
| Toluene | 320.0 | 40.6 |
| Pyridine | 347.0 | 55.6 |
| Cyclohexane | 280.0 | 40.2 |
| Decalin | 391.0 | 25.8 |
| Cyclohexanol | 356.0 | 38.0 |
| o-Xylene | 357.0 | 35.0 |
| Tetralin | 446.0 | 34.7 |

One compound that is particularly well suited for use with the present invention is carbon dioxide ($CO_2$). Carbon dioxide is preferred because it is nonflammable, reasonably priced, and is easily separated or removed from the constituents used in making orthopedic parts at the contemplated temperatures and pressures. Therefore, there will be no residual $CO_2$ in the finished products that could contribute to problems in use. The particular process medium employed to produce a particular orthopedic part can vary depending on such factors as the availability and cost of the medium, safety concerns, and working pressures and temperatures.

Although different process media may be used to produce the orthopedic mixtures in accordance with the principles of the present invention, care must be taken not to utilize starting materials that are soluble in the process medium at operating temperatures and pressures. If the starting materials are soluble in the process medium, it will not be possible to transfer the starting materials to the mold 14 without losing some of the starting materials to the storage tank 22, which would be a very undesirable result.

Starting materials that are used in the present invention are a source of calcium ions and a matrix for the calcium source. Optionally, additives such as growth factors or nutrients can be used. Because the orthopedic mixtures produced by the present invention are used in the human body, potentially harmful additives such as pigments, flow control agents, extenders, and the like should not be used.

Suitable sources of calcium ions include calcium phosphate ($Ca_3(PO_4)_2$), calcium hydroxy apatite ($3Ca_3(PO_4)2*Ca(OH)_2$), tri-basic calcium phosphate ($Ca_{10}(OH)_2(PO_4)_6$), durapatite ($3Ca_3(PO_4)2*Ca(OH)_2$), calcium salts of condensed phosphates, calcium sulfate ($CaSO_4$), gypsum hemi-hydrate and gypsum dihydrate. Salts of calcium acetate and other organic calcium salts also can be used, including monovalent, divalent, and multivalent complexes. Chelated complexes of calcium such as calcium edetate (EDTA) or other chelates of calcium may be used.

The matrix for the source of calcium ions is provided by a polymer, either thermoplastic, thermoset, or a combination of both. Polymers suitable for use in controlled drug release are discussed in K. Ulrich, et al., Polymeric Systems for Controlled Drug Release, Journal of the American Chemical Society (1999)("the Polymer Article"). It is believed that such polymers are suitable for use with the present invention. As noted in the Polymer Article, categories of suitable polymers include polyesters, polyorthoesters, polyanhydrides, polyamides, and phosphorous-containing polymers. It has been found that hydroxy-methyl cellulose and derivative-type polymers (e.g., hydroxy propyl cellulose) and polylactide-co-glycolide (e.g., Medisorb 8515 DL High I.V.) function well as part of the present invention. Other suitable polymers as specified in the Polymer Article include polyethylene, polypropylene, polyvinyl chloride, polyvinyl alcohol, polyethylene-vinyl acetate, polyenolketone, polyacrylic acid, polycarbophil, polyacrylamides, poly-N-isopropyl acrylamide, polyacrylates, polyethylene glycol, polyglycolic acid, polylactic acid, poly-$\epsilon$-caprolactone, poly-3-hydroxybutyrate, polyortho esters, polyanhydrides, polyamino acids, pseudo-polyamino acids, polyamide-enamines, polyamido amines, polyurethanes, azopolymers, polydimethylsiloxane, and polyphosphazenes.

When $CO_2$ gas is utilized as a process medium, $CO_2$ is charged to or utilized in reactor 12 so as to provide from about 10% by weight to about 90% by weight $CO_2$ and from about 90% by weight to about 10% by weight starting materials, preferably from about 20% by weight to about 80% by weight $CO_2$ and from about 80% by weight to about 20% by weight starting materials, and more preferably from about 40% by weight to about 60% by weight $CO_2$ and from about 60% by weight to about 40% by weight starting materials. After processing, the materials in mold 14 are a collection of homogeneous, uniformly sized particles. In the unlikely event that any oversize particles or an agglomeration of particles (foam) are contained in mold 14, the molded part must be rejected.

The following Examples describe a method of producing an orthopedic part within the scope of the present invention. Unless otherwise indicated, all parts and percentages are by weight and all temperatures are in degrees Centigrade (°C.). For purposes of facilitating a better understanding of the invention, the following examples make reference to the various elements of FIG. 1.

EXAMPLE 1

Two hundred eighty (280) grams of a 50:50 mixture of calcium sulfate ($CaSO_4$) and poly-$\epsilon$- caprolactone (PCL) was charged into a one-gallon reactor 12. Reactor 12 was filled with 2.49 kilograms of liquid $CO_2$ from source 16. The source 16 of $CO_2$ is a standard commercial source maintained at a temperature of about −18° C. and a pressure of about 20 bar. The filled reactor 12 was heated to 38° C. at a pressure of 116 bar, thereby rendering the $CO_2$ a supercritical fluid. The starting materials and supercritical fluid were maintained under these conditions while being mixed for one hour using agitation device 34. The mixer 40 was rotated at a rate of 150 rpm. After one hour, the temperature was increased to 75° C. and 245 bar. Mixing was continued for an additional 20 minutes at 150 rpm.

Upon completion of mixing as described, the starting materials were formed into a supercritical fluid slurry. The valve 26 was opened and the slurry was directed through a conduit 13 having a diameter of 0.63 centimeter into the mold 14. The part cavity 44 has an inner diameter of about 1.26 centimeters and a length of about 15.2 centimeters. The mold 14 was filled instantly, producing a solid rod with a very dense surface and a somewhat porous core.

The experiment was repeated with a lower pressure of 184 bar in the final stage of reaction. Suitable material ranges for the $CaSO_4$ starting material are 1–99% and 20–99% for the PCL polymer starting material. The pressure in the reactor 12 can be varied between 13.6–986 bar, the temperature can vary between 0–127° C., and the mixing rate can vary between 1–150 rpm.

EXAMPLE 2

One hundred (100) grams of a 50:50 mixture of tri-basic calcium phosphate ($CA_{10}(OH)_2(PO_4)_6$) ($Ca_3(PO_4)_2$) and PCL was loaded into a one-gallon reactor 12 with a volume-reducing, conical insert. The reactor 12 was connected to a multi-cavity mold having cavities 58 to form cubic parts. Reactor 12 was filled with 2.2 kilograms of liquid $CO_2$ from source 16. The filled reactor 12 was heated to 90° C. and a pressure of 218 bar, thereby rendering the $CO_2$ a supercritical fluid. The starting materials and supercritical fluid were maintained under these conditions while being mixed for one hour using agitation device 34. The mixer 40 was rotated at a rate of 40 rpm.

Upon completion of mixing as described, the starting materials were formed into a supercritical fluid slurry. As in Example .1, the valve 26 was opened and the slurry was directed through the conduit 13 into mold 14 where solidification occurred quickly.

The experiment was reproduced easily many times. Suitable material ranges for the $CA_{10}(OH)_2(PO4)_6$ starting material are 1–80% and 20–99% for the PCL polymer starting material. The pressure in the reactor 12 can be varied between 13.6986 bar, the temperature can vary between 0–127° C., and the mixing rate can vary between 1–150 rpm.

EXAMPLE 3

Two hundred (200) grams of a 40:60 mixture of $CA_{10}(OH)_2(PO_4)_6$ and PCL was loaded into a one-gallon reactor 12 with a volume-reducing conical insert. The reactor 12 was connected to a multi-cavity mold 14 having cavities 58 to form cubic parts. Reactor 12 was filled with 2.500 kilograms of liquid $CO_2$ from source 16. The filled reactor 12 was heated to 90° C. at a pressure of 222 bar, thereby rendering the $CO_2$ a supercritical fluid. The starting materials and supercritical fluid were maintained under these conditions while being mixed for one hour using agitation device 34. The mixer 40 was rotated at a rate of 40 rpm.

Upon completion of mixing as described, the starting materials were formed into a supercritical fluid slurry. As in Example 1, the valve 26 was opened and the slurry was directed through the conduit 13 into the mold 14 where solidification occurred quickly.

The experiment was reproduced easily several times. A mold 14 having a different interconnectivity pattern between the cubic cavities was installed and molding was completed successfully under slightly varied mixing conditions, specifically, 90° C. reactor temperature, 227 bar reactor pressure, and 50 rpm mixer speed. Pressure dropped less than 6.8 bar during transfer of the material into the mold 14. Suitable material ranges for the $CA_{10}(OH)_2(PO_4)_6$ starting material are 1% and 80% for the PCL polymer starting material are 20% to 90%. The pressure in the reactor 12 can be varied between 13.6–986 bar, the temperature can vary between 32–200° C., and the mixing rate can vary between 1–150 rpm.

EXAMPLE 4

Fifty-one (51) grams of a 20:80 mixture of calcium hydroxy apatite (FAST FLOW) and polylactide-co-glycolide (Medisorb 8515 DL High l.V.) (PLGA) was loaded into a one-gallon reactor 12 with a volume-reducing, conical insert. The reactor 12. was connected to a multi-cavity mold 14 having cavities 58 to form cubic parts. Reactor 12 was filled with 2.6 kilograms of liquid $CO_2$ from source 16. The filled reactor 12 was heated to 105° C. and pressure of 231 bar, thereby rendering the $CO_2$ a supercritical fluid. The starting materials and supercritical fluid were maintained under these conditions while being mixed for one hour using agitation device 34. The mixer 40 was rotated at a rate of 50 rpm.

Upon completion of mixing as described, the starting materials were formed into a supercritical fluid slurry. As in Examples 1 and 2, the valve 26 was opened and the slurry was directed through the conduit 13 into the mold 14. In contrast to the previous examples, the mold cavities were only partially filled, indicating excessively viscous material. The solution to excessive viscosity is to raise the temperature in the reactor 12.

Suitable material ranges for the starting calcium salt material are 1% and 80% for the PLGA polymer starting material 20% to 99%. The pressure in the reactor 12 can be varied between 20–1000 bar, the temperature can vary between 0–133° C., and the mixing rate can vary between 1–150 rpm.

Although the invention has been described in its preferred form with a certain degree of particularity, it will be understood that the present disclosure of the preferred embodiment has been made only by way of example, and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A method for manufacturing an orthopedic part, comprising:
   providing a reactor having a mixer;
   providing a mold that has a cavity of a shape suitable to form an orthopedic part;
   providing a conduit that connects the reactor and the mold;
   charging the reactor with starting materials that include a source of calcium ions and a matrix for the calcium ions;
   providing supercritical fluid in the reactor;
   mixing the starting materials and the supercritical fluid in the reactor for a period of time sufficient to form a supercritical fluid slurry;
   transferring the slurry from the reactor into the mold through the conduit; and permitting the slurry to solidify in the cavity.

2. The method of claim 1, wherein the supercritical fluid is selected from the group consisting of carbon dioxide, water, nitrous oxide, methane, ethane, ethylene, propane, pentane, benzene, methanol ethanol, isopropanol, various fluorocarbons such as cholrotrifluoromethane and monofluoromethane, toluene, pyridine, cyclohexane, decalin, cyclohexanol, o-xylene, and tetralin.

3. The method of claim 1, wherein the step of providing supercritical fluid in the reactor is accomplished by charging a liquid into the reactor, and thereafter heating and pressurizing the reactor contents so that the liquid attains a supercritical state.

4. The method of claim 3, wherein the liquid is carbon dioxide.

5. The method of claim 4, wherein the carbon dioxide is heated to a temperature within the range of 32–133° C. and is pressurized to a pressure within the range of 72–400 bar.

6. The method of claim 1, wherein, during the step of mixing, the reactor is maintained at a temperature below the melting point of the starting materials.

7. The method of claim 1, wherein at least a portion of the supercritical fluid is vented from the mold as the step of transferring is occurring.

8. The method of claim 1, wherein the source of calcium ions is selected from the group consisting of calcium hydroxy apatite, tri-basic calcium phosphate, calcium salts of condensed phosphates, calcium sulfate, gypsum hemihydrate, gypsum dihydrate, monovalent, divalent, and multivalent complexes of salts of calcium acetate and other organic calcium salts, calcium edetate and other chelated complexes of calcium.

9. The method of claim 1, wherein the matrix for the calcium ions is a thermoplastic polymer, a thermoset polymer, or a combination of thermoplastic and thermoset polymers.

10. The method of claim 9, wherein the matrix is selected from the group consisting of hydroxy-methyl cellulose and its derivatives, polylactide-co-glycolide, polyethylene, polypropylene, polyvinyl chloride, polyvinyl alcohol, polyethylene-vinyl acetate, polyenol-ketone, polyacrylic acid, polycarbophil, polyacrylamides, poly-N-isopropyl acrylamide, polyacrylates, polyethylene glycol, polyglycolic acid, polylactic acid, poly-$\epsilon$-caprolactone, poly-3-hydroxybutyrate, polyortho esters, polyanhydrides, polyamino acids, pseudo-polyamino acids, polyamide-enamines, polyamido amines, polyurethanes, azopolymers, polydimethylsiloxane, and polyphosphazenes.

11. The method of claim 1 further comprising the step of providing an orifice in the conduit.

12. The method of claim 11, wherein the orifice has a diameter within the range of about 0.0254 centimeter to about 0.254 centimeter.

13. The method of claim 1, further comprising the step of providing a nozzle having multiple openings in the conduit.

14. The method of claim 13, wherein the openings in the nozzle have a diameter within the range of about 0.0524 centimeter to about 0.254 centimeter.

15. The method of claim 1, wherein the step of mixing is accomplished by a blade or helical mixer.

16. The method of claim 15, wherein the mixer is rotated at a speed within the range of 1–150 rpm.

17. An orthopedic part produced by the method of claim 1.

* * * * *